United States Patent
Wisdom et al.

(10) Patent No.: US 12,369,544 B2
(45) Date of Patent: Jul. 29, 2025

(54) RICE CULTIVAR 'ARoma 22'

(71) Applicant: The Board of Trustees of the University of Arkansas, Little Rock, AR (US)

(72) Inventors: Debra Ahrent Wisdom, Southaven, MS (US); Karen A. K. Moldenhauer, Garnavillo, IA (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 359 days.

(21) Appl. No.: 17/974,059

(22) Filed: Oct. 26, 2022

(65) Prior Publication Data

US 2024/0138333 A1  May 2, 2024

(51) Int. Cl.
*A01H 6/46* (2018.01)
*A01H 5/10* (2018.01)

(52) U.S. Cl.
CPC ............. *A01H 6/4636* (2018.05); *A01H 5/10* (2013.01)

(58) Field of Classification Search
None
See application file for complete search history.

(56) References Cited

U.S. PATENT DOCUMENTS

| | | |
|---|---|---|
| 6,281,416 B1 | 8/2001 | Moldenhauer |
| 7,429,697 B2 | 9/2008 | Moldenhauer |
| 8,134,058 B2 | 3/2012 | Moldenhauer |
| 9,398,750 B2 | 7/2016 | Moldenhauer |
| 9,877,452 B1 | 1/2018 | Moldenhauer |
| 10,791,697 B2 * | 10/2020 | Wisdom .................. A01H 5/10 |
| 2022/0095561 A1 | 3/2022 | Moldenhauer |
| 2022/0104447 A1 | 4/2022 | Moldenhauer |
| 2022/0125000 A1 | 4/2022 | Sha |
| 2022/0132766 A1 | 5/2022 | Moldenhauer |

OTHER PUBLICATIONS

Moldenhauer, K.A.K., et al. 2009. 'Taggart', High Yielding Large Kernel Long-Grain Rice Variety. in: Norman, R.J et al., Rice Research Studies 2008. University of Arkansas Agricultural Experiment Station Research Series 571. pp. 68-73.
Sha, X.Y., et al. Registration of 'Jazzman' Aromatic Long-Grain Rice. Journal of Plant Registrations 5:304-308 (2011).
Moldenhauer, K.A.K., et al. Registration of 'Drew' Rice. Crop Science 38:896-897 (1998).
PI 637517 (IRGA 417). 1998. Donated by International Center for Tropical Agriculture (CIAT). U.S. National Plant Germplasm System. [retrieved on Nov. 2017]. Retrieved from: https://npgsweb.ars-grin.gov/gringlobal/accessiondetail?id=1570364.
U.S. Plant Variety Protection Application No. 202300078 filed Dec. 8, 2022, Rice Cultivar Aroma 22, The Board of Trustees of the University of Arkansas.

* cited by examiner

*Primary Examiner* — Brent T Page
*Assistant Examiner* — Aleksandar Radosavljevic
(74) *Attorney, Agent, or Firm* — Quarles & Brady, LLP

(57) ABSTRACT

A rice cultivar designated ARoma 22 is disclosed herein. The present invention provides seeds, plants, and plant parts derived from rice cultivar ARoma 22. Further, it provides methods for producing a rice plant by crossing ARoma 22 with itself or another rice variety. The invention also encompasses any rice seeds, plants, and plant parts produced by the methods disclosed herein, including those in which additional traits have been transferred into ARoma 22 through the introduction of a transgene or by breeding ARoma 22 with another rice cultivar.

20 Claims, No Drawings

RICE CULTIVAR 'ARoma 22'

BACKGROUND OF THE INVENTION

The present invention relates to a new and distinctive rice cultivar, designated ARoma 22.

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valley of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season. In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in regions where rice is drill-seeded and a water-seeded nursery is used in regions where water-seeding is prominent.

Rice in the United States is classified into three primary market types by grain size, shape and chemical composition of the endosperm: long-grain, medium-grain, and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated ARoma 22. The invention encompasses the seeds, plants, and plant parts of rice cultivar ARoma 22, as well as plants with all the physiological and morphological characteristics of ARoma 22.

This invention also provides methods for producing a rice plant by planting a plurality of seeds or by crossing rice cultivar ARoma 22 with itself or another rice line. Any plant breeding methods using rice cultivar ARoma 22 are part of this invention, including selfing, backcrosses, hybrid production, and crosses to populations. All plants and seeds produced using rice cultivar ARoma 22 as a parent are within the scope of this invention, including gene-converted plants of ARoma 22. Methods for introducing a gene into ARoma 22, either through traditional breeding or transformation, are also provided herein.

In still another aspect, the present invention provides regenerable cells for use in tissue culture of rice plant ARoma 22, as well as rice plants regenerated from these tissue cultures.

Definitions

To provide a clear and consistent understanding of the specification and claims, the following definitions are provided:

Allele. One of two or more alternative forms of a gene, all of which relate to a single trait or characteristic. In a diploid cell or organism, two alleles of a given gene occupy corresponding loci on a pair of homologous chromosomes.

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be backcrossed with one of the parental lines used to produce the $F_1$ hybrids.

Breeding. The genetic manipulation of living organisms.

Cell. A cell is the basic structural unit of all organisms. As used herein, this term includes isolated cells, cells grown in tissue culture, and cells that comprise a plant or plant part.

Cultivar. Used interchangeably with "variety". Refers to plants that have been cultivated by humans that have the characteristics of a particular genotype or combination of genotypes. Plants of a particular cultivar are distinguished from any other plants by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem, and leaves.

Essentially all or all the physiological and morphological characteristics. A plant having essentially all the physiological and morphological characteristics of the cultivar exhibits the characteristics of the cultivar with the exception of any characteristics derived from a converted gene.

$F_\#$. Denotes a filial generation, wherein the # is the generation number. For example, $F_1$ is the first filial generation.

Gene. Refers to a unit of inheritance corresponding to a distinct DNA sequence that forms part of a chromosome. A gene may encode a polypeptide or a functional nucleic acid molecule.

Gene-converted. Describes a plant wherein essentially all the desired physiological and morphological characteristics of a parental variety are maintained with the exception of a single trait that was transferred into the variety via back-crossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernal length (L). Length of a rice grain measured in millimeters.

Kernal width (W). Width of a rice grain measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength."

Milling yield. A measure of the amount of rice kernels recovered after milling (i.e., the removal of hulls, bran, and germ). Milling yield is often expressed as a ratio of the amount of head rice (i.e., whole kernels) to the total amount of milled rice (i.e., whole and broken kernels). Both values are expressed as a weight percentage of the original paddy or rough rice sample that was milled. For example, for a sample of 100 grams of rough rice, a milling yield of 65:70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an $F_1$ rice plant produced from the cross of two rice plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like.

Trait. Refers to a measurable and/or observable characteristic of an organism.

Transgenic. Describes an organism or cell that contains genetic material that has been artificially introduced.

Wild-type. Used to refer to a gene that is common throughout a population and is, thus, arbitrarily designated the "normal" or "wild-type" form of the gene.

DETAILED DESCRIPTION OF THE INVENTION

The present invention provides a novel rice cultivar designated ARoma 22. The invention encompasses both the seeds of this cultivar and plants grown from these seeds. The invention further encompasses any rice plant having essentially all the physiological and morphological characteristics rice cultivar ARoma 22.

Development and Characterization of Rice Cultivar ARoma 22:

ARoma 22 (*Poaceae Oryzea Oryza sativa* L.) is a high yielding, mid-season, jasmine-type aromatic long-grain rice cultivar. ARoma 22 originated from the cross 'Jazzman'// 'Drew'/'PI 637517"/3/'Taggart' made in 2012. Jazzman is a high yielding, conventional height, jasmine-type aromatic, long-grain rice with very good milling and excellent grain quality. Jazzman was developed in Crowley, LA and described by Sha and Linscombe in 2011. Drew is an early long-grain variety with excellent resistance to blast and very good yield potential. PI 637517 (IRGA 417) is a plant introduction donated by the International Center for Tropical Agriculture, Brazil (CIAT) in 1998. Taggart (U.S. Pat. No. 8,134,058) is a midseason long-grain with very high yield potential and good milling yield.

The experimental designation for early evaluation of ARoma 22 was STG16L-15-043, starting with a bulk of $F_5$ seed from the 2016 panicle row L-15-043. ARoma 22 was tested in the Arkansas Rice Performance Trials (ARPT) from 2020 to 2021 and in the Cooperative Uniform Regional Rice Nursery (URRN) from 2019 to 2021 as entry RU1901231 (RU stands for Cooperative Uniform Regional Rice Nursery; 19 indicates that the year entered was 2019; 01 is the Stuttgart, AR designation; and 231 identifies the entry number).

ARoma 22 is similar in maturity to 'RU1401105' (U.S. Pat. No. 10,791,697) at 88 days to 50% heading. ARoma 22 has excellent straw strength, comparable to that of RU1401105. Both ARoma 22 and RU1401105 received a 1.0 rating in the 2020 ARPT data (straw strength scale 0=very strong straw, 5=very weak straw). The plant height of ARoma 22 ranges from 38 (25%) to 43 (75%) inches and the canopy height of ARoma 22 is 38 inches. Thus, ARoma 22 is slightly taller than RU1401105 which has a plant height of 41 inches and a canopy height of 36 inches. The level of the compound 2-acetyl-1-pyrroline (2AP) is used as a quantification of aroma in rice. ARoma 22 was found to have a higher level of 2AP (431 ng/g) than RU1401105 (264 ng/g) as tested in 2019.

Rough rice yields of ARoma 22 have been consistently excellent in the ARPT. In 5 ARPT yield trials from 2020, the average yields of ARoma 22, RU1901206, and RU1401105 were 167, 180, and 167 bushels/acre (12% moisture), respectively. Data from the URRN conducted in Arkansas, Louisiana, Missouri, Mississippi, and Texas from 2019 to 2020 indicates that the average grain yield of ARoma 22, RU1901206, and RU1401105 was 169.1, 179.5, and 171.4 bushels/acre, respectively. Milling yields (mg g$^{-1}$ whole kernel:mg g$^{-1}$ total milled rice at 120 mg g$^{-1}$ moisture) from the 2020 ARPT, averaged 640:710, 610:690, 650:710 for ARoma 22, RU1901206, and RU1401105, respectively. The milling yields from the URRN Arkansas trials from 2019 to 2020 averaged 620:700, 620:690, and 630:710 for ARoma 22, RU1901206, and RU1401105, respectively.

In most cases, ARoma 22, like RU1401105, 'Jazzman-2,' and Taggart, is moderately susceptible to common races of rice blast (*Pyricularia grisea* (Cooke) Sacc.). ARoma 22 is rated moderately susceptible to sheath blight (*Rhizoctonia solani* Kühn), which compares favorably with RU1401105 (MS), Jazzman-2 (S), 'Della-2' (S), and Taggart (MS), using the standard disease scale: R=resistant, MR=moderately resistant, MS=moderately susceptible, S=susceptible, and VS=very susceptible to disease. Under high nitrogen fertilization, ARoma 22 is susceptible to false smut (*Ustilaginoidea virens* (Cooke) Takah). ARoma 22 is rated moderately susceptible for bacterial panicle blight (*Burkholderia glumae*), which compares favorably with RU1401105 (MS), Jazzman-2 (VS), Della-2 (MS), and Taggart (MS). Reactions to straighthead, narrow brown leaf spot, stem rot, black sheath rot, and sheath spot are currently unknown.

Plants of ARoma 22 have erect culms, green erect leaves, and pubescent lemma, palea, and leaf blades. The lemma and palea are straw colored with purple apiculi, many of which fade to straw at maturity. Individual milled kernel weights of ARoma 22, RU1901206, and RU1401105 averaged 22.3, 22.7, and 21.3 g/1,000 seeds milled rice, respectively, in the 2020 ARPT (5 locations, 2 replications/test).

The endosperm of ARoma 22 is nonglutinous, aromatic, and covered by a light brown pericarp. Rice quality parameters indicate that ARoma 22 has jasmine-type characteristics as described by Webb et. al. 1985. ARoma 22 has an average apparent starch amylose content of 16.4 g kg$^{-1}$ as compared to RU1901206 and RU1401105 which have average apparent starch amylose contents of 22.0 and 15.8 g kg$^{-1}$, respectively. The intermediate gelatinization temperatures of ARoma 22, RU1901206, and RU1401105 are 61.9, 69.0, and 62.4° C., respectively, according to the data from the Riceland Quality Laboratory. ARoma 22 has excellent whiteness and low chalk ratings.

The foundation seed field of ARoma 22 was rogued several times throughout the season. The variants that may be found in the release include any combination of the following: taller, shorter, earlier, later, glabrous or pubescent plants, non-aromatic, and intermediate or very-long slender grains. Other atypical plants may still be encountered in the variety. The total variants and/or off-types numbered less than 1 per 2,000 plants.

The above-mentioned characteristics of rice cultivar ARoma 22 are based primarily on data collected in Stuttgart, Arkansas and are summarized in Table 1. The developmental timeline for ARoma 22 is shown in Table 2. The results of the rice performance trials (ARPT 2020-2021 and URRN 2019-2021) are detailed in Tables 3-22. Disease evaluation data is shown in Table 23.

TABLE 1

Cultivar description information

Plant:

Grain type: Long
Days to maturity (Seeding to 50% heading): 88
Plant height: 96-111 cm
Plant color at booting: Green
Culm:

Angle (degrees from perpendicular after flowering): Erect (less than 30°)
Flag leaf (after heading):

Pubescence: Glabrous
Leaf angle: Erect
Blade color: Green
Panicle:

Length: 23.3 cm (range 19-28 cm)
Type: Intermediate
Exertion (near maturity): Moderately well
Axis: Droopy
Shattering (at maturity): Low (1-5%)
Grain (spikelet):

Awns (after full heading): Absent
Apiculus color: Purple
Stigma color: Purple
Lemma and palea color (at maturity): Straw
Lemma and palea pubescence: Short hairs
Grain (seed):

Seed coat color: Light brown
Scent: Scented
Shape class (length/width ratio):

Paddy: Long (3.4:1 and more)
Brown: Long (3.1:1 and more)
Milled: Long (3.0:1 and more)
Size: 22.3 g/1000 seeds milled rice
Disease resistance:

Rice blast (*Pyricularia grisea* (Cooke) Sacc.): Moderately susceptible
Sheath blight (*Rhizoctonia solani* Kuhn): Moderately susceptible
False smut (*Ustilaginoidea virens* (Cooke) Takah.): Moderately susceptible
Bacterial panicle blight (*Burkholderia glumae* and *B. gladioli*): Moderately susceptible
Narrow brown leaf spot (*Cerospora oryzae*): Moderately resistant

TABLE 2

Development timeline of ARoma 22

| Year | Program Stage |
|---|---|
| 2021 | Arkansas Rice Performance Trials (6 locations) and URRN (5 locations) acre Foundation Seed Field, Stuttgart AR |
| 2020 | Arkansas Rice Performance Trials (5 locations) and URRN (5 locations) Breeder Head rows, Stuttgart AR |
| 2019 | Arkansas Rice Performance Trials (4 locations) and URRN (5 locations) Advanced Yield Trials (1 location), Stuttgart, AR |
| 2018 | Preliminary Trials (1 location), Stuttgart, AR |
| 2017 | Preliminary Trials (1 location), Stuttgart, AR |
| 2016 | F6 L Panicle row (single row) harvested in bulk and designated STG16L-15-043, Stuttgart, AR |
| 2015 | F5 L Panicle row (single row) Stuttgart, AR |
| 2014 | F$_4$ P Panicle row (single row) Stuttgart, AR |
| 2013-14 winter | F3 Panicle row (single row), Puerto Rico |
| 2013 | F$_2$ grown in Field UADA, RREC, Stuttgart |
| 2012-13 winter | F1 plants are grown in the greenhouse in Stuttgart, AR |
| 2012 | Cross Number 20123405, Jazzman//Drew/PI 637517/3/Taggart |

TABLE 3

2020 ARPT data (Stuttgart, RREC; Keiser, NERES; Colt, PTRS; Clay Co.; and Desha Co.)

| VARIETY | YIELD (BU/AC) | HEIGHT (IN.)^ | MATURITY (50% HD) | KERNEL WT (mg)* | MILLING HR:TOT* |
|---|---|---|---|---|---|
| ARoma 22 | 167 | 38.8 | 82 | 22.3 | 64:71 |
| RU1901206 | 180 | 33.4 | 84 | 22.7 | 61:69 |
| RU1401105 | 167 | 36.3 | 82 | 21.3 | 65:71 |

*Milling data collected from RREC, PTES, Clay Co., and Desha Co. test plots

TABLE 4

2021 ARPT data (Stuttgart, RREC; Keiser, NEREC; Colt, PTRS; and Jonesboro, NERice)

| VARIETY | YIELD (BU/AC) | HEIGHT (IN.)^ | MATURITY (50% HD) | KERNEL WT (mg)# | MILLING HR:TOT# |
|---|---|---|---|---|---|
| ARoma 22 | 173 | 37.6 | 98 | | |
| RU1901206 | 184 | 32.5 | 102 | | |
| RU1401105 | 170 | 35.9 | 100 | | |

Milling data not available as of October 2021
^Plant height measured to canopy and not to tip of panicle

TABLE 5

2020-2021 average ARPT data (9 Tests: Stuttgart (2), Keiser (2), Pine Tree (2), Jonesboro (1), Clay Co. (1), and Desha Co. (1))

| VARIETY | YIELD (BU/AC) | HEIGHT (IN.)^ | MATURITY (50% HD) | KERNEL WT (MG)* | MILLING HR:TOT* |
|---|---|---|---|---|---|
| ARoma 22 | 170 | 38.2 | 90 | | |
| RU1901206 | 182 | 33.0 | 93 | | |
| RU1401105 | 169 | 36.1 | 91 | | |

*Milling data collected from RREC in 2020, 2021; NEREC in 2020, 2021; PTES in 2020, 2021; Clay County in 2020; Desha County in 2020; and NERice in 2021
^Plant height measured to canopy and not to tip of panicle

TABLE 6

2020 ARPT grain yield means by location

| | GRAIN YIELD (BU/AC) | | | | | |
|---|---|---|---|---|---|---|
| VARIETY | RREC | NEREC | PTES | CLAY CO | DESHA CO | AVG |
| ARoma 22 | 122 | 171 | 153 | 214 | 176 | 167 |
| RU1901206 | 166 | 161 | 161 | 227 | 182 | 180 |
| RU1401105 | 145 | 163 | 156 | 217 | 154 | 167 |

TABLE 7

2020 ARPT milling yield means by location

| | HEAD RICE (%):TOTAL RICE (%)* | | | | | |
|---|---|---|---|---|---|---|
| VARIETY | RREC | NEREC | PTES | CLAY CO | DESHA CO | AVG |
| ARoma 22 | 64:71 | 65:71 | 64:71 | 64:72 | 64:70 | 64:71 |
| RU1901206 | 64:70 | 63:70 | 63:70 | 55:59 | 58:68 | 61:69 |
| RU1401105 | 67:71 | 65:71 | 67:72 | 65:72 | 64:70 | 65:71 |

TABLE 8

2020 ARPT amylose content means by location

| | AMYLOSE (G/KG)* | | | | | |
|---|---|---|---|---|---|---|
| VARIETY | RREC | NEREC | PTES | CLAY CO | DESHA CO | AVG |
| ARoma 22 | 13.16 | 16.52 | 17.04 | 17.97 | 15.51 | 16.04 |
| RU1901206 | 19.91 | 22.36 | 24.52 | 22.54 | 20.72 | 22.01 |
| RU1401105 | 16.01 | 16.31 | 16.21 | 16.09 | 14.49 | 15.82 |

TABLE 9

2020 ARPT gelatinization temperature means by location

| | GEL TEMP (° C.)* | | | | | |
|---|---|---|---|---|---|---|
| VARIETY | RREC | NEREC | PTES | CLAY CO | DESHA CO | AVG |
| ARoma 22 | 61.05 | 61.20 | 62.16 | 61.79 | 63.07 | 61.85 |
| RU1901206 | 69.17 | 68.37 | 68.63 | 68.42 | 70.20 | 68.96 |
| RU1401105 | 61.03 | 61.38 | 65.86 | 61.39 | 62.51 | 62.43 |

TABLE 10

2021 ARPT grain yield means by location

| | GRAIN YIELD (BU/AC) | | | | |
|---|---|---|---|---|---|
| VARIETY | RREC | NEREC | PTES | NERice | AVG |
| ARoma 22 | 179 | 185 | 141 | 188 | 173 |
| RU1901206 | 186 | 207 | 159 | 186 | 184 |
| RU1401105 | 181 | 184 | 132 | 184 | 170 |

TABLE 11

2019 Arkansas URRN data

| VARIETY | YIELD (BU/AC) | HEIGHT (IN.) | MATURITY (50% HD) | MILLING HR:TOT |
|---|---|---|---|---|
| ARoma 22 | 149.6 | 42.5 | 86 | 63:71 |
| RU1901206 | 191.1 | 38.2 | 91 | 63:71 |
| RU1401105 | 181.7 | 35.0 | 90 | 62:72 |

TABLE 12

2020 Arkansas URRN data

| VARIETY | YIELD (BU/AC) | HEIGHT (IN.) | MATURITY (50% HD) | MILLING HR:TOT |
|---|---|---|---|---|
| ARoma 22 | 156.0 | 44.1 | 90 | 61:68 |
| RU1901206 | 175.4 | 39.4 | 92 | 60:67 |
| RU1401105 | 166.9 | 40.2 | 90 | 64:70 |

TABLE 13

2021 Arkansas URRN data - preliminary

| VARIETY | YIELD (BU/AC) | HEIGHT (IN.) | MATURITY (50% HD) | MILLING HR:TOT |
|---|---|---|---|---|
| ARoma 22 | 171.7 | 43.7 | 86 | |
| RU1901206 | 190.9 | 39.0 | 91 | |
| RU1401105 | 203.1 | 41.7 | 89 | |

TABLE 14

2019-2021 Arkansas URRN data - preliminary

| VARIETY | YIELD (BU/AC) | HEIGHT (IN.) | MATURITY (50% HD) | MILLING HR:TOT* |
|---|---|---|---|---|
| ARoma 22 | 159.1 | 43.4 | 87 | 62:70 |
| RU1901206 | 185.7 | 38.9 | 91 | 62:69 |
| RU1401105 | 183.9 | 39.0 | 90 | 63:71 |

*Average milling yields are based on two years data reported in 2019 and 2020

TABLE 15

2019 URRN grain yield means by location

| | GRAIN YIELD (BU/AC) | | | | | |
|---|---|---|---|---|---|---|
| VARIETY | AR | LA | MO | MS | TX | AVG |
| ARoma 22 | 149.6 | 170.3 | 183.8 | 170.0 | 144.4 | 163.6 |
| RU1901206 | 191.1 | 177.7 | 166.7 | 188.4 | 137.7 | 172.3 |
| RU1401105 | 181.7 | 168.0 | 187.0 | 163.2 | 126.2 | 165.2 |

TABLE 16

2019 URRN milling yield means by location

| | HEAD RICE (%):TOTAL RICE (%) | | | | | |
|---|---|---|---|---|---|---|
| VARIETY | AR | LA | MO | MS | TX | AVG |
| ARoma 22 | 63:71 | 66:71 | 68:73 | 64:71 | 50:65 | 62:70 |
| RU1901206 | 63:71 | 63:71 | 62:72 | 64:70 | 51:65 | 60:70 |
| RU1401105 | 62:72 | 65:71 | 69:73 | 67:71 | 58:66 | 64:71 |

TABLE 17

2020 URRN grain yield means by location

| | GRAIN YIELD (BU/AC) | | | | | |
|---|---|---|---|---|---|---|
| VARIETY | AR | LA | MO | MS | TX | AVG |
| ARoma 22 | 156.0 | 163.1 | 168.1 | 212.8 | 173.0 | 174.6 |
| RU1901206 | 175.4 | 208.4 | 153.5 | 210.2 | 185.3 | 186.6 |
| RU1401105 | 166.9 | 181.3 | 172.2 | 160.3 | 206.9 | 177.5 |

TABLE 18

2020 URRN milling yield means by location

| | HEAD RICE (%):TOTAL RICE (%) | | | | | |
|---|---|---|---|---|---|---|
| VARIETY | AR | LA | MO | MS | TX | AVG |
| ARoma 22 | 61:68 | 66:72 | No data | 60:70 | 51:66 | 59:69 |
| RU1901206 | 60:67 | 65:71 | No data | 62:71 | 57:66 | 61:69 |
| RU1401105 | 64:70 | 69:73 | No data | 59:70 | 61:68 | 63:70 |

TABLE 19

2021 URRN grain yield means by location - preliminary

| | GRAIN YIELD (BU/AC) | | | | | |
|---|---|---|---|---|---|---|
| VARIETY | AR | LA | MO | MS | TX | AVG |
| ARoma 22 | 171.7 | 149.2 | | | | |
| RU1901206 | 190.9 | 168.6 | | | | |
| RU1401105 | 203.1 | 169.3 | | | | |

TABLE 20

Riceland Quality Laboratory ARPT data 2020 for ARoma 22

| Location | Rep | Chalk | Length | Width | Thickness | L:W Ratio | Kernel weight | Gel temp | Amylose |
|---|---|---|---|---|---|---|---|---|---|
| Clay | 1 | 2.03 | 7.46 | 2.13 | 1.68 | 3.5 | 22.1 | 61.9 | 17.54 |
| Clay | 3 | 1.03 | 7.4 | 2.18 | 1.68 | 3.39 | 21.7 | 61.68 | 18.4 |
| Desha | 1 | 0.87 | 7.27 | 2.1 | 1.68 | 3.46 | 20.9 | 63.14 | 16.33 |
| Desha | 3 | 1.55 | 7.63 | 2.13 | 1.72 | 3.58 | 22.6 | 63 | 14.69 |
| NEREC | 1 | 0.79 | 7.56 | 2.15 | 1.72 | 3.52 | 22.5 | 61.08 | 16.81 |
| NEREC | 3 | 0.77 | 7.56 | 2.2 | 1.68 | 3.44 | 23.8 | 61.31 | 16.23 |
| PTRS | 1 | 0.54 | 7.47 | 2.06 | 1.7 | 3.63 | 22.1 | 62.06 | 17.4 |
| PTRS | 3 | 0.86 | 7.62 | 2.15 | 1.71 | 3.54 | 23.5 | 62.25 | 16.68 |
| RREC | 1 | X | X | X | X | X | X | X | X |
| RREC | 3 | 0.63 | 7.5 | 2.12 | 1.69 | 3.54 | 21.6 | 61.05 | 13.16 |
| Avg | | 1.01 | 7.5 | 2.14 | 1.7 | 3.51 | 22.3 | 61.94 | 16.36 |

| Location | Rep | RVA | | | | | Satake Whiteness | Milling degree |
|---|---|---|---|---|---|---|---|---|
| | | Peak | Trough | Breakdown | Final | Setback | | |
| Clay | 1 | 220 | 100 | 120 | 239 | 19 | 37.3 | 83 |
| Clay | 3 | 245 | 123 | 122 | 273 | 28 | 35.9 | 77 |
| Desha | 1 | 247 | 123 | 124 | 265 | 18 | 36.5 | 79 |
| Desha | 3 | 225 | 116 | 109 | 267 | 42 | 31.2 | 50 |
| NEREC | 1 | 258 | 130 | 128 | 265 | 8 | 37.3 | 82 |
| NEREC | 3 | 241 | 120 | 121 | 254 | 13 | 38.9 | 89 |
| PTRS | 1 | 255 | 115 | 139 | 259 | 5 | 39.8 | 96 |
| PTRS | 3 | 251 | 114 | 138 | 254 | 3 | 36.6 | 81 |
| RREC | 1 | X | X | X | X | X | X | X |
| RREC | 3 | 250 | 129 | 121 | 260 | 9 | 36.5 | 79 |
| Avg | | 243 | 119 | 125 | 260 | 16 | 36.7 | 80 |

TABLE 21

Average kernel characteristics from
the 2019 ARPT RREC yield trial

| Variety | Length (mm) | Width (mm) | Thickness (mm) | L/W Ratio | Kernel Weight (mg) |
|---|---|---|---|---|---|
| ARoma 22 | No Data | No Data | No Data | No Data | No Data |
| RU1901206 | 7.71 | 2.11 | 1.68 | 3.66 | 22.3 |
| RU1401105 | 7.28 | 2.14 | 1.72 | 3.40 | 21.8 |

TABLE 22

Average kernel characteristics from
the 2020 ARPT RREC yield trial

| Variety | Length (mm) | Width (mm) | Thickness (mm) | L/W Ratio | Kernel Weight (mg) |
|---|---|---|---|---|---|
| ARoma 22 | 7.50 | 2.14 | 1.70 | 3.51 | 22.3 |
| RU1901206 | 7.82 | 2.13 | 1.69 | 3.67 | 22.7 |
| RU1401105 | 7.30 | 2.13 | 1.69 | 3.43 | 21.3 |

Disease Evaluations of Rice Cultivar ARoma 22:

Varietal resistance is the most efficient and reliable means of controlling rice diseases. Conservation and improvement of disease resistance is a continuous endeavor basic to varietal development. Incorporation of existing and new resistance sources is a complex process limited by several variables. The rice disease research program routinely evaluates breeding program entries to provide disease data required for superior variety development. Our objectives are to increase varietal disease resistance and to define disease liabilities of new varieties released for rice production in Arkansas.

Rice diseases are mostly rated visually on a 0-9 scale to estimate degree of severity. Numerical data is often converted to this scale. A rating of zero indicates complete disease immunity. A rating of one to three indicates resistance where little loss occurs and in the case of rice blast pathogen growth is restricted considerably. Conversely, a nine rating indicates maximum disease susceptibility, which typically results in near complete plant death and/or yield loss. Depending upon the disease in question, a disease rating of four to six is usually indicative of acceptable disease resistance under conditions slightly favoring the pathogen. Numerical ratings are sometimes converted to letter symbols where 0-3=R (resistant), 3-4=MR (moderately resistant), 5-6=MS (moderately susceptible), 7=S (susceptible), and 8-9 VS (very susceptible). Exceptions to established ratings do occur unexpectedly as disease situations change.

These data come from several sources. Advanced and promising breeding lines are normally evaluated by researchers in other states. It is not unusual for ratings to vary with location and year due to environmental differences and research procedures. Ratings within a source traditionally have been consistent.

Greenhouse blast tests are the primary means of screening large number of entries for varietal reaction to the many blast races occurring in the production areas. Although results are quite variable and testing conditions tend to overwhelm any field resistance present in the entry, this test provides an accurate definition of the fungus-variety genetics. Blast field nurseries utilizing both natural and lab produced inoculum are established to better define blast susceptibility under field conditions.

Field nurseries are established and artificially inoculated to provide a uniform disease pressure for evaluations under field conditions. Grower nurseries are established and operated to evaluate disease reactions in grower fields under current production practices. Over time these nurseries document variety performance under adverse disease conditions in Arkansas production fields.

Below, Table 23 shows disease evaluation data collected by Dr. Wamishe.

TABLE 23

| | Rice variety reactions[1] to diseases | | | | | | | |
|---|---|---|---|---|---|---|---|---|
| Cultivar | Sheath Blight | Leaf Blast | Panicle/ Neck Blast | Straighthead | Bacterial Panicle Blight | Narrow Brown Leaf Spot | Kernel Smut | False Smut |
| ARoma 22 | MS | MS | MS | — | MS | MR | — | MS |
| RU1901206 | MS | MS | MS | — | S | MS | — | — |
| RU1401105 | MS | MS | — | S | MS | — | S | S |

[1]Reaction:
R = Resistant;
MR = Moderately Resistant;
MS = Moderately Susceptible;
S = Susceptible;
VS = Very Susceptible.
Reactions were determined based on historical and recent observations from test plots and grower fields across Arkansas and other rice states in southern USA.
In general, these ratings represent expected cultivar reactions to disease under conditions that most favor severe disease development.

Methods:

This present invention provides methods for producing rice plants. In some embodiments, these methods involve crossing a first parent rice plant with a second parent rice plant, wherein either the first or second parent rice plant is an ARoma 22 rice plant. Further, both the first and second parent rice plants can come from rice cultivar ARoma 22. This invention is also directed to methods for producing an ARoma 22-derived rice plant by crossing rice cultivar ARoma 22 with a second rice plant, growing the progeny seed, and repeating the crossing and growing steps with the ARoma 22-derived plant from 0 to 7 times. Any such methods using rice cultivar ARoma 22 are part of this invention, including selfing, backcrosses, hybrid production, crosses to populations, and the like. All plants produced using rice cultivar ARoma 22 as a parent are within the scope of this invention, including plants derived from rice cultivar ARoma 22. In some embodiments, rice cultivar ARoma 22 is used in crosses with other, different, rice cultivars to produce first generation (F$_1$) rice seeds and plants with superior characteristics.

In some embodiments, an ARoma 22 progeny plant is selected that has molecular markers, morphological characteristics, and/or physiological characteristics in common with ARoma 22 (e.g., those listed in Table 1). Techniques such as RFLP-enhanced selection, genetic marker enhanced selection (e.g., SSR markers), and the making of double haploids may be utilized to identify progeny that share particular traits with ARoma 22.

Further, this invention provides methods for introducing a desired trait into rice cultivar ARoma 22. This may be accomplished using traditional breeding methods, such as backcrossing (see the section titled "Breeding Methods" below). Alternatively, the desired trait may be introduced by transforming the rice cultivar with a transgene (see the section title "Transformation Methods" below). The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps that involve producing rice seed from the resulting rice plants and/or planting the rice seed.

The present invention encompasses all plants and parts thereof produced by the methods described herein, as well as the seeds produced by these plants. Further, any plants derived from rice cultivar ARoma 22 or produced from a cross using cultivar ARoma 22 are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar ARoma 22 comprising a combination of at least two traits of ARoma 22 selected from those described in the Tables and Detailed Description of the Invention. The progeny rice plant should not be significantly different from ARoma 22 for said traits, as determined at the 5% significance level when grown in the same environment. Those of skill in the art know how to compare a trait between two plant varieties to determine if there is a significant difference between them (Fehr and Walt, Principles of Cultivar Development, pp. 261-286 (1987)). Molecular markers or mean trait values may be used to identify a plant as progeny of ARoma 22. Alternatively, progeny may be identified through their filial relationship with rice cultivar ARoma 22 (e.g., as being within a certain number of breeding crosses of rice cultivar ARoma 22). For example, progeny produced by the methods described herein may be within 1, 2, 3, 4, or 5 breeding crosses of rice cultivar ARoma 22.

Tissue Culture:

The present invention provides tissue cultures of regenerable cells or protoplasts produced from rice cultivar ARoma 22. As is well known in the art, tissue culture of rice can be used for the in vitro regeneration of a rice plant. Thus, such cells and protoplasts may be used to produce plants having all the physiological and morphological characteristics of rice variety ARoma 22. The rice plants regenerated by these methods are also encompassed by the present invention.

As used herein, the term "tissue culture" describes a composition comprising isolated plant cells or a collection of such cells organized into parts of a plant. Exemplary tissues for culture include protoplasts, calli, plant clumps, embryos, pollen, flowers, seeds, pods, leaves, stems, roots, root tips, and anthers. Culture of various rice tissues and regeneration of plants therefrom is well known in the art.

Breeding Methods:

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar ARoma 22 in any plant breeding method is encompassed by the present invention. The choice of a breeding or selection method will depend on several factors, including the mode of plant reproduction, the heritability of the trait(s) being improved, and the type of cultivar used commercially (e.g., F$_1$ hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an F$_1$ population. An F$_2$ population is produced by selfing one or several F$_1$'s. Selection of the best individuals may begin in the F$_2$ population; then, beginning in the F$_3$ generation, the best individuals in the best families are selected. Replicative testing of families can begin in the F$_4$ generation to make selection of traits with low heritability more effective. At an advanced stage of inbreeding (e.g., F$_6$ or F$_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods:

As is noted above, the present invention provides plants and seeds of rice cultivar ARoma 22 in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is a DNA molecule comprising a gene operatively linked to a regulatory element (e.g., a promoter) that drives its expression in a cell. The expression vector may contain one or more such gene/regulatory element combinations. The expression vector may also include additional sequences, such as a signal sequence or a tag, that modify the protein produced by the transgene.

Expression vectors typically include at least one genetic marker that allows transformed cells containing the vector to be recovered by selection. In some embodiments, negative selection (i.e., inhibiting the growth of cells that do not contain the selectable marker gene) is utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and green fluorescent protein (GFP).

Transgene expression is typically driven by operably linking the transgene to a promoter within the expression vector. However, other regulatory elements may also be used to drive transgene expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be tissue-specific, cell type-specific, inducible, or constitutive. Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement,* 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch, et al., *Science,* 227:1229 (1985). Descriptions of *Agrobacterium* vector systems and methods for *Agrobacterium*-mediated gene transfer are provided by Gruber, et al., supra.

REFERENCES

Moldenhauer, K. A. K., K. A. Gravois, F. N. Lee, R. J. Norman, J. L. Bernhardt, B. R. Wells, R. H. Dilday, M. M. Blocker, P. C. Rohman, and T. A. McMinn. 1998. Registration of 'Drew' Rice. Crop Science 38:896-897.

Moldenhauer, K. A. K., J. W. Gibbons, F. N. Lee, J. L. Bernhardt, C. E. Wilson, Jr., R. D. Cartwright, R. J. Norman, M. M. Blocker, D. K. Ahrent, V. A. Boyett, J. M. Bulloch, and E. Castaneda. 2009. 'Taggart', High Yielding Large Kernel Long-Grain Rice Variety. In R. J. Norman, J. F. Meullenet, and K. A. K. Moldenhauer (eds.) Rice Research Studies 2008. University of Arkansas Agricultural Experiment Station Research Series 571. pp. 68-73.

PI 637517 (IRGA 417). 1998. Donated by International Center for Tropical Agriculture (CIAT). U.S. National Plant Germplasm System. Access date: November 2017. Available at: www.npgsweb.ars-grin.gov Sha, X. Y., S. D. Linscombe, F. Jodari, Q. R. Chu, D. E. Groth, S. B. Blanche, D. L. Harrell, L. M. White, J. H. Oard, M. H. Chen, S. Theunissen, and B. J. Henry. 2011. Registration of 'Jazzman' Aromatic Long-Grain Rice. Journal of Plant Registrations 5:304-308.

Webb, B. D., C. N. Bollich, H. L. Carnahan, K. A. Kuenzel., and K. S. Mckenzie. 1985. Utilization characteristics and qualities of United States rice. p. 25-35. In: Rice grain quality and marketing. IRRI, Manila, Philippines

DEPOSIT INFORMATION

A deposit of the University of Arkansas Division of Agriculture Rice Research and Extension Center proprietary rice cultivar 'ARoma 22' disclosed above and recited in the appended claims has been made with the Provasoli-Guillard National Center for Marine Algae and Microbiota (NCMA) (60 Bigelow Drive, East Boothbay, Me. 04544) and has been accepted under the terms of the Budapest Treaty. The date of deposit was May 1, 2023. The deposit of 625 seeds was taken from the same deposit maintained by the University of Arkansas Division of Agriculture Rice Research and Extension Center (2900 Hwy 130 E., Stuttgart, AR 72160) since prior to the filing date of this application. All restrictions will be irrevocably removed upon granting of a patent, and the deposit is intended to meet all of the requirements of 37 C.F.R. §§ 1.801-1.809. The Accession Number provided by the International Depository Authority is 202305001. The deposit will be maintained in the depository for a period of thirty years, or five years after the last request, or for the enforceable life of the patent, whichever is longer, and will be replaced as necessary during that period.

What is claimed is:

1. A rice seed of the cultivar 'ARoma 22', a representative sample of seed of said cultivar having been deposited under National Center for Marine Algae and Microbiota International Depository Authority Accession No. 202305001.

2. A rice plant, or a part thereof, produced by growing the seed of claim 1.

3. A rice plant, or a part thereof, having all the physiological and morphological characteristics of the rice plant of claim 2.

4. Pollen or an ovule of the plant of claim 2.

5. A method for producing rice plants, said method comprising planting a plurality of rice seeds as recited in claim 1 under conditions favorable for the growth of rice plants.

6. The method of claim 5, further comprising the step of producing rice seed from the resulting rice plants.

7. A rice seed produced by the method of claim 6.

8. A tissue culture of regenerable cells or protoplasts produced from the rice plant of claim 2.

9. The tissue culture of claim 8, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

10. A rice plant regenerated from the tissue culture of claim 8, said rice plant having all the physiological and morphological characteristics of 'ARoma 22'.

11. A method for producing an $F_1$ hybrid rice plant, said method comprising crossing a first parent rice plant with a second parent rice plant, wherein the first parent rice plant or the second patent rice plant is the rice plant of claim 2.

12. The method of claim 11, further comprising the step of producing rice seed from the resulting rice plant.

13. A rice seed produced by the method of claim 12.

14. The method of claim 11, wherein the second parent rice plant is transgenic.

15. A method comprising transforming the rice plant of claim 2 or cell thereof with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

16. A rice plant or part thereof, or rice seed, produced by the method of claim 15.

17. An herbicide resistant rice plant produced by the method of claim 15, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

18. A method of introducing a desired trait into rice cultivar 'ARoma 22', said method comprising the steps of:
(a) crossing plants as recited in claim 2 with plants of another rice line expressing the desired trait, to produce progeny plants;
(b) selecting progeny plants that express the desired trait, to produce selected progeny plants;
(c) crossing the selected progeny plants with plants from the 'ARoma 22' parental line to produce new progeny plants;
(d) selecting new progeny plants that express the desired trait; and
(e) repeating steps (c) and (d) three or more times in succession to produce selected higher generation backcross progeny plants that express the desired trait.

19. The method of claim 18, additionally comprising the step of planting a plurality of rice seed produced by selecting higher generation backcross progeny plants under conditions favorable for the growth of rice plants and optionally comprising the step of producing rice seed from the resulting rice plants.

20. The rice seed resulting from the method of claim 19, wherein, if the resulting rice seed is grown, then the rice plants grown from the resulting rice seed express the desired trait.

\* \* \* \* \*